United States Patent [19]

Schwertfeger

[11] Patent Number: 4,940,814
[45] Date of Patent: Jul. 10, 1990

[54] REACTION OF HEXAFLUOROPROPENE OXIDE WITH FLUORINATED CARBOXYLIC ACID FLUORIDES

[75] Inventor: Werner Schwertfeger, Langgöns, Fed. Rep. of Germany

[73] Assignee: Hoechst Aktiengesellschaft, Frankfurt am Main, Fed. Rep. of Germany

[21] Appl. No.: 163,691

[22] Filed: Mar. 3, 1988

[30] Foreign Application Priority Data

Mar. 7, 1987 [DE] Fed. Rep. of Germany ....... 3707367

[51] Int. Cl.$^5$ ............................................. C07C 51/58
[52] U.S. Cl. .................................................. 562/849
[58] Field of Search ...................... 260/544 P; 562/849

[56] References Cited

U.S. PATENT DOCUMENTS

| | | | |
|---|---|---|---|
| 3,250,807 | 5/1966 | Fritz et al. | 562/849 |
| 3,274,239 | 9/1966 | Selman | 260/544 P |
| 3,301,893 | 1/1967 | Putman et al. | 260/544 P |
| 4,329,434 | 5/1982 | Kimoto et al. | 562/849 |
| 4,329,435 | 5/1982 | Kimoto et al. | 562/849 |
| 4,345,092 | 8/1982 | Resnick | 560/182 |
| 4,510,328 | 4/1985 | Kimoto et al. | 562/849 |
| 4,511,518 | 4/1985 | Kimoto et al. | 562/849 |
| 4,536,352 | 8/1985 | Kimoto et al. | 562/849 |
| 4,555,369 | 11/1985 | Kimoto et al. | 562/849 |
| 4,597,913 | 7/1986 | Kimoto et al. | 562/849 |
| 4,613,467 | 9/1986 | Kimoto et al. | 562/849 |

FOREIGN PATENT DOCUMENTS

| | | |
|---|---|---|
| 1234702 | 2/1967 | Fed. Rep. of Germany . |
| 3050634 | 4/1981 | Fed. Rep. of Germany . |
| 1342515 | 9/1963 | France . |
| 1038193 | 8/1966 | United Kingdom . |

OTHER PUBLICATIONS

H. Millauer et al, *Angew. Chem. Int. Ed., Engl.* 24:161–179 (1985).

*Primary Examiner*—Paul J. Killos

[57] ABSTRACT

Process for the preparation of halogenated carboxylic acid fluorides, in which a carboxylic acid fluoride is reacted with hexafluoropropene oxide in the presence of a catalyst system composed of an alkali metal fluoride, a carboxylic acid dinitrile and at least one ether of the formula $$CH_3O-(CH_2CH_2O)_z-CH_3 \qquad (V)$$

in which z denotes an integer from 2 to 6.

15 Claims, No Drawings

REACTION OF HEXAFLUOROPROPENE OXIDE WITH FLUORINATED CARBOXYLIC ACID FLUORIDES

Fluorinated acid fluorides of the general formula $$R_f\text{-}(CF_2\text{-}O\text{-}\underset{\underset{CF_3}{|}}{CF})_n\text{-}COF \quad (I)$$

in which $R_f$ denotes a halogen-containing, in most cases fluorine-containing, radical, preferably perfluoroalkyl, branched or unbranched and having 1-10 carbon atoms and n denotes an integer from 1 to 5 are prepared by reacting carboxylic acid fluorides of the general formula $$R_f\text{---COF} \quad (II)$$

in which $R_f$ has the abovementioned meaning with hexafluoropropene oxide (HFPO). The reaction is carried out in the presence of a catalyst and takes place in accordance with the following equation.

$$R_f\text{---COF} + n\ CF_3\text{---}\underset{\underset{}{}}{CF}\overset{O}{\underset{}{\diagdown}}CF_2 \xrightarrow{\text{[catalyst]}}$$

$$R_f\text{-}(CF_2\text{-}O\text{-}\underset{\underset{CF_3}{|}}{CF})_n\text{-}COF$$

A summarizing description of this reaction, including the catalysts used, has been given in Angew. Chem. Int. Ed. Engl. 24, 161-178 (1985). One of the catalysts described therein is a mixture of potassium fluoride/adiponitrile and tetraglyme (tetraethylene glycol dimethyl ether). The mixture has hitherto only been employed for the synthesis of special compounds of the general formula (I), for example $$CF_3\text{-}CF_2\text{-}CF_2\text{-}O\text{-}\underset{\underset{CF_2N_3}{|}}{CF}\text{-}(CF_2\text{-}O\text{-}\underset{\underset{CF_3}{|}}{CF})_n\text{-}COF \quad (a)$$

$$CH_3OOC\text{-}CF_2\text{-}(CF_2\text{-}O\text{-}\underset{\underset{CF_3}{|}}{CF})_n\text{-}COF \quad (b)$$

or $$CH_3\text{-}O\text{-}CF_2\text{-}CF_2\text{-}(CF_2\text{-}O\text{-}\underset{\underset{CF_3}{|}}{CF})_n\text{-}COF \quad (c)$$

(EP-A 0,070,635,
DE-A 3,130,859,
EP-A 0,150,618).

One advantage of this catalyst mixture is stated to be a maximum yield of the desired product of the general formula (I), with the simultaneous avoidance of by-products of the type $$CF_3\text{-}CF_2\text{-}(CF_2\text{-}O\text{-}\underset{\underset{CF_3}{|}}{CF})_m\text{-}COF \quad m = 0\text{-}5,$$

which are formed by the reaction of HFPO with itself. It is stated as a further advantage of this catalyst system that potassium fluoride, which is cheap, can be employed as the source of fluoride ions.

The yields of the desired compounds of the general formula (I) were, however, below 50% when this catalyst system was employed, so that its use cannot in general be regarded as advantageous.

The reaction of acid fluorides of the general formula $$R\text{---COF} \quad (III)$$

in which R is the group $CCl_3$ or $X\text{-}(CF_2)_p$, X being hydrogen, bromine or $SO_2F$ and p being an integer from 1 to 6, with HFPO has hitherto been carried out in accordance with the instructions in the presence of catalysts containing costly cesium fluoride (Angew. Chem. Int. Ed. Engl. 24, 161 (1985)).

It was therefore required to find a catalyst system which can be employed generally for this reaction and which can replace the expensive cesium fluoride and which enables good utilization of the HFPO.

The invention relates to a process for the preparation of halogenated carboxylic acid fluorides by reacting a carboxylic acid fluoride with hexafluoropropene oxide in the presence of a catalyst, in which process a carboxylic acid fluoride of the formula $$R\text{---COF} \quad (III)$$

in which R is the group $CCl_3$ or $X\text{-}(CF_2)_n$, X representing a hydrogen atom, a bromine atom or a fluorosulfonate radical and n denoting an integer from 1 to 6, is reacted with hexafluoropropene oxide in the presence of a catalyst system composed of an alkali metal fluoride, a carboxylic acid dinitrile and at least one ether of the formula $$CH_3O\text{-}(CH_2CH_2O)_z\text{-}CH_3 \quad (V)$$

in which z denotes an integer from 2 to 6.

It is preferable to employ a carboxylic acid fluoride of the formula (III) in which R has the meaning mentioned above and n denotes an integer from 2 to 4.

It was surprising that the catalyst system employed in accordance with the invention produces high conversions of the acid fluoride of the general formula (III), gives a high utilization of HFPO and can be employed generally and then gives yields which are markedly higher than the yields hitherto achieved in the case of certain compounds or at least achieves the yields which it was possible to achieve using the cesium fluoride catalysts.

In addition, the reaction system is substantially less sensitive to moisture than the other known systems. The yields achieved are, in general, between 65 and 80%. The acid fluorides obtained by the process according to the invention are valuable intermediate products in the field of the organic chemistry of fluorine. In particular, they are employed for the preparation of vinyl ethers of the general formula $$R\text{-}CF_2\text{-}(O\text{-}\underset{\underset{CF_3}{|}}{CF}\text{-}CF_2)_q\text{-}O\text{-}CF=CF_2 \quad (IV)$$

in which R has the abovementioned meaning and q can be an integer from 0 to 2.

The catalyst system used is a mixture of an alkali metal fluoride, a carboxylic acid dinitrile and at least one ether of the formula (V). Alkali metal fluorides are sodium fluoride and, preferably, potassium fluoride. The carboxylic acid dinitrile used can be the dinitriles of saturated aliphatic dicarboxylic acids having 5 to 8 carbon atoms, preferably adipodinitrile. Ethers of the formula (V) are polyethylene glycol dimethyl ether, preferably the dimethyl ether of triethylene or pentaethylene glycol, but particularly the tetra-compound (tetraglyme). The three components of the catalyst system are employed in the ratio (5–30):(50–80):(5–40), preferably (8–20):(55–70):(10–30) percent by weight, relative to the system. It is advantageous for the alkali metal fluoride to be thoroughly dried and finely pulverized before use. A carboxylic acid dinitrile of commercially available purity can be used without further pretreatment. The ether, for example tetraglyme, can also be employed without further treatment in the purity available. It is also possible to use tetraglyme in the form of a distillation cut composed of oligomeric ethylene glycol dimethyl ethers together with the main component tetraglyme. It is also not disadvantageous for the reaction according to the invention if the tetraglyme contains a small amount of the monomethyl ether component. Thus, for example, the tetraglyme used in Example 1 is composed of 17% area of triglyme, 65% area of tetraglyme, 12% area of pentaglyme, 1% area of hexaglyme and 5% area of triglycol monomethyl ether, determined by gas chromatography. The catalyst system is used in an amount of 5 to 45, preferably 10 to 40, % by weight, relative to the carboxylic acid fluoride employed.

The reaction according to the invention is carried out by initially placing the catalyst mixture in a vessel which can, for example, be made of glass or stainless steel and which is equipped with an effective stirrer, and adding the acid fluoride of the general formula (III). The required amount of HFPO is then introduced in the form of gas. It is advantageous to stir vigorously during the whole reaction. The reaction can be carried out under reduced pressure, elevated pressure or normal pressure, but normal pressure or elevated pressure, in general up to 20 bar, preferably up to 10 bar, is preferred. The reaction temperature can be between −30 and +100° C., temperatures between 0° and 60° C. being preferable.

EXAMPLES (1) 90 g of potassium fluoride, 350 ml of adiponitrile and 100 ml of tetraglyme (wide boiling range) were put into a 5 liter glass autoclave equipped with a stirrer, and 2,050 g of $H-CF_2-CF_2-COF$ were introduced into the mixture. HFPO was then injected, with vigorous stirring, whereupon an exothermic reaction set in. The pressure was kept at 2–3.5 bar and the internal temperature at 40°-50° C. Altogether, 2,900 g of HFPO were reacted. The mixture was stirred overnight at room temperature, in the course of which the pressure fell to less than 0.5 bar. The contents of the autoclave were subjected to simple distillation. This gave 4,430 g of a colorless distillate which had a boiling point of 30°-130° C. and which, according to gas chromatography on a sample esterified with methanol had the following composition:

|  |  | % by weight | b.p. | yield* |
|---|---|---|---|---|
| $CF_3-CF_2+CF_2-O-CF\!\!\mid_{\overline{m}}COF$ with $CF_3$ branch | m = 1 | 11 | 55–58° C. | discarded |
|  | m = 2 | 1 | 116–120° C. | |
| $H-(CF_2)_2+CF_2-O-CF\!\!\mid_{\overline{n}}COF$ with $CF_3$ branch | n = 1 | 70 | 72–75° C. | 71% |
|  | n = 2 | 16 | 126–130° C. | 11% |
|  | n = 3 | 1 | | |

*relative to $H-CF_2-CF_2-COF$ employed

The conversion of $H-CF_2-CF_2-COF$ was over 90%.

(2) (Comparison) A catalyst mixture composed of 30 g of cesium fluoride and 100 ml of tetraglyme as well as 880 g of $H-CF_2-CF_2-COF$ was initially placed in a 2 liter glass autoclave equipped with a stirrer, and was reacted as in Example 1 with 1,975 g of HFPO at 23°-29° C. and a pressure of 3.2–3.6 bar. A residual pressure of 1.6 bar was still present after stirring overnight. Working up as in Example 1 gave the following yields:

| | | | | |
|---|---|---|---|---|
| $CF_3-CF_2+CF_2-O-CF\!\!\mid_{\overline{m}}COF$ with $CF_3$ branch | m = 1 | b.p. 55–58° C. | 520 g | |
|  | m = 2 | b.p. 116–120° C. | 223 g | |
| $H-(CF_2)_2+CF_2-O-CF\!\!\mid_{\overline{n}}COF$ with $CF_3$ branch | n = 1 | b.p. 72–75° C. | 1,067 g | 57% |
|  | n = 2 | b.p. 126–130° C. | 556 g | 20% |

The conversion of $H-CF_2-CF_2-COF$ was approx. 90%.

(3) 1,416 g of $Br-CF_2-COF$, 50 g of potassium fluoride, 300 ml of adiponitrile and 120 ml of tetraglyme were initially placed in the apparatus of Example 1. The exothermic reaction with 1,550 g of HFPO is carried out at 45°-50° C. and a pressure of 2–2.2 bar. When the introduction of HFPO was complete, the pressure fell rapidly to 0 bar. Distillation of the contents of the autoclave gave the following: 2,106 g of the compound

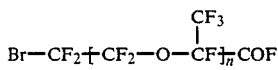

in which n = 1 (=77%), b.p. 71°-76° C. and 62 g of the compound in which n = 2 (=1.5%), b.p. 128° C.

(4) 15 g of potassium fluoride, 100 ml of adiponitrile and 40 ml of tetraglyme were initially placed in a glass flask equipped with a refrigerated condenser (−78° C.), a thermometer and a gas inlet tube. This mixture was cooled and 788 g of Br—CF$_2$—CF$_2$—COF previously cooled to −5° C. were added. 680 g of HFPO were then introduced in the form of gas under normal pressure in the course of 415 minutes, and the internal temperature of the mixture was kept below 50° C. The following acid fluorides were isolated by distillation:

| | b.p. | | |
|---|---|---|---|
| Br—(CF$_2$)$_2$—CF$_2$—O—CF(CF$_3$)—COF | 97–99° C., | 1,065 g | 78% |
| Br—(CF$_2$)$_2$—[CF$_2$—O—CF(CF$_3$)—]$_2$COF | 147° C., | 151 g | 8% |

(5) 90 g of potassium fluoride, 350 ml of adipodinitrile and 100 ml of tetraglyme were initially placed in a glass flask equipped as in Example 4. 2,465 g of CF$_2$—CF$_2$—O—SO$_2$ were then added dropwise, and this isomerized immediately, in an exothermic reaction, to give FSO$_2$—CF$_2$—COF. 4,370 g of HFPO were then introduced in the form of gas and the internal temperature was kept below 50° C. during the introduction of the gas. The mixture was worked up by distillation. 3,745 g (79%) of FSO$_2$—CF$_2$—CF$_2$—O—CF(CF$_3$)—COF having a boiling point of 92°–94° C. were obtained.

(6) 29 g of potassium fluoride, 150 ml of adipodinitrile, 60 of tetraglyme and 1,400 g of CCl$_3$—COF were initially placed in an apparatus as described in Example 4. 1,660 g of HFPO were then introduced in the form of gas in the course of 4.5 hours, the internal temperature being kept below 37° C. by cooling. The reaction mixture was subjected to a distillation under reduced pressure in which the internal temperature was kept below 120° C. Crude yield of acid fluoride mixtures 2,950 g. Fractional distillation under normal pressure gave the following yields:

| | | b.p. | | |
|---|---|---|---|---|
| CCl$_3$—[CF$_2$—O—CF(CF$_3$)—]$_n$COF | n = 1 | 117–121° C., | 1,924 g | 68.6% |
| | n = 2 | 161–163° C., | 169 g | 4% |

(7) 5 g of potassium fluoride, 50 ml of adipodinitrile and 20 ml of tetraglyme were initially placed in the apparatus of Example 4 and 203 g of 5-H-octafluorovaleryl fluoride were added dropwise. 166 g of HFPO were introduced in the form of gas in the course of 40 minutes, and the internal temperature was kept at 25°–40° C. by cooling with ice. Stirring was continued for one hour at room temperature, and the mixture was distilled under reduced pressure, whereby 317 g of distillate having a boiling point of 43°–83° C./67 mbar were obtained. 39 g of substance condensed in the cold trap (−78° C.) situated downstream. The distillate and the contents of the trap were combined. The composition was determined by esterifying a sample with methanol. The mixture of esters showed the following composition when subjected to analysis by gas chromatography:

approx. 4% area    CF$_3$—CF$_2$—CF$_2$—O—CF(CF$_3$)—COOCH$_3$ approx. 4% area n = 0
approx. 80% area n = 1      H—(CF$_2$)$_4$—[CF$_2$—O—CF(CF$_3$)]$_n$—COOCH$_3$
approx. 8% area n = 2

240.5 g (≅71%) of H—(CF$_2$)$_5$—O—CF(CF$_3$)—COF, b.p. 115°–119° C., were isolated by distillation through a packed column.

I claim
1. A process for the preparation of halogenated carboxylic acid fluorides by reacting a carboxylic acid fluoride with hexafluoropropene oxide in the presence of a catalyst, which comprises reacting a carboxylic acid fluoride of the formula

$$R—COF \qquad (III)$$

in which is the group CCl$_3$ or X—(CF$_2$)$_n$, X representing a hydrogen atom, a bromine atom or a fluorosulfonate radical and n denoting an integer from 1 to 6, with hexafluoropropene oxide in the presence of a catalyst system comprising an alkali metal fluoride, a carboxylic acid dinitrile and at least one ether of the formula $$CH_3O—(CH_2CH_2O)_z—CH_3 \qquad (V)$$

in which z denotes an integer from 2 to 6.

2. The process as claimed in claim 1, wherein the carboxylic acid fluoride used is a compound of the formula (III) in which R has the meaning mentioned, but in which n denotes 2, 3 or 4.

3. The process as claimed in claim 1, wherein the alkali metal fluoride used is potassium fluoride.

4. The process as claimed in claim 1, wherein the carboxylic acid dinitrile used is a dinitrile of a saturated aliphatic dicarboxylic acid having 5 to 8 carbon atoms.

5. The process as claimed in claim 4, wherein the carboxylic acid dinitrile used is adipodinitrile.

6. The process as claimed in claim 1, wherein the ether of the formula (2) used is the dimethyl ether of triethylene, tetraethylene or pentaethylene glycol.

7. The process as claimed in claim 1, wherein the reaction is carried out at a temperature from −30° to +100° C.

8. The process as claimed in claim 7, wherein the reaction is carried out at a temperature between 0° and 60° C.

9. The process as claimed in claim 1, wherein the components of the catalyst system are used in an amount composed of 5 to 30 % by weight of alkali metal fluoride, 50 to 80 % by weight of carboxylic acid dinitrile and 5 to 40 % by weight of ether, in each case relative to the catalyst system.

10. The process as claimed in claim 9, wherein the components are employed in the ratio (8–20):(55–70):(10–30).

11. The process as claimed in claim 1, wherein the catalyst system is used in an amount of 5 to 45 % by weight, relative to the carboxylic acid fluoride.

12. The process as claimed in claim 11, wherein an amount of 10 to 40 % by weight of the catalyst is used.

13. A process for the preparation of halogenated carboxylic acid fluorides which comprises:

reacting a carboxylic acid fluoride of the formula $$R-COF \quad (III)$$

in which R is $CCl_3$ or $X-(CF_2)_n$,
wherein X is H, Br, or $FSO_2$,
and n is an integer from 1 to 6, with hexafluoropropene oxide in the presence of a catalyst system consisting essentially of:
(a) potassium fluoride,
(b) a carboxylic acid dinitrile, and
(c) at least one ether of the formula $$CH_3O-(CH_2CH_2O)_z CH_3$$

in which z is an integer from 2 to 6.

14. A process as claimed in claim 13, wherein the dinitrile is a dintrile of a saturated aliphatic dicarboxylic acid having 5 to 8 carbon atoms.

15. A process as claimed in claim 13, wherein the catalyst system consists essentially, based on the weight of said catalyst system, of:
(a) 5–30% by weight potassium fluoride,
(b) 50–80% by weight adiponitrile, and
(c) 5–40% of said ether.

* * * * *

UNITED STATES PATENT AND TRADEMARK OFFICE
CERTIFICATE OF CORRECTION

PATENT NO. : 4,940,814
DATED : July 10, 1990
INVENTOR(S) : WERNER SCHWERTFEGER

It is certified that error appears in the above-identified patent and that said Letters Patent is hereby corrected as shown below:

In Claim 1, Col. 6, line 27 please insert -- R -- after "which".

In Claim 10, Col. 7, lines 2-3

"(8-20):(55-70):(- 10-30)"

should read

-- (8-20):(55-70):(10-30) -- .

Signed and Sealed this

Fifth Day of November, 1991

*Attest:*

HARRY F. MANBECK, JR.

*Attesting Officer*     *Commissioner of Patents and Trademarks*